United States Patent [19]

Alperovich et al.

[11] Patent Number: 4,823,790

[45] Date of Patent: * Apr. 25, 1989

[54] CRYOGENIC-AND-ULTRASONIC SCALPEL

[76] Inventors: Boris I. Alperovich, ulitsa Dzerzhinskogo, 36, kv. 47; Ljutsia Paramonova, ulitsa Ferentsa Mjunnikha, 3, kv. 25; Gennady Tjulkov, ulitsa Nakhimova, 15, kv. 142; Valery I. Soloviev, pereulok Krasnogo pozharnika, 5, kv. 4; Alexandr I. Paramonov, ulitsa Ferentsa Mjunnikha, 3, kv. 25, all of Tomsk, U.S.S.R.

[*] Notice: The portion of the term of this patent subsequent to Feb. 16, 2005 has been disclaimed.

[21] Appl. No.: 55,168

[22] Filed: May 28, 1987

Related U.S. Application Data

[63] Continuation-in-part of Ser. No. 900,457, Aug. 26, 1986, Pat. No. 4,724,834.

[30] Foreign Application Priority Data

Nov. 20, 1985 [SU] U.S.S.R. .................................. 3973881

[51] Int. Cl.⁴ .............................................. A61B 17/36
[52] U.S. Cl. .................................................. 128/303.1
[58] Field of Search .................... 128/24 A, 241, 24.2, 128/303.1, 399–402, DIG. 27; 73/642

[56] References Cited

U.S. PATENT DOCUMENTS

| | | | |
|---|---|---|---|
| 3,636,943 | 1/1972 | Balamuth | 128/303.1 |
| 3,786,814 | 1/1974 | Armao | 128/303.1 |
| 3,918,442 | 11/1975 | Nikolaev et al. | 128/303.1 |
| 3,942,519 | 3/1976 | Shock | 128/303.1 |
| 4,528,979 | 7/1985 | Marchenko et al. | 128/303.1 |
| 4,609,368 | 9/1986 | Dotson | 128/24 A |

FOREIGN PATENT DOCUMENTS

| | | | |
|---|---|---|---|
| 460869 | 4/1975 | U.S.S.R. | 128/303.1 |
| 556797 | 6/1977 | U.S.S.R. | 128/303.1 |
| 825056 | 4/1981 | U.S.S.R. | . |
| 1153901 | 5/1985 | U.S.S.R. | 128/303.1 |

OTHER PUBLICATIONS

"Cryosurgery Imaging with Ultrasound" Rubinsky et al. Mechanical Engineering Jan. 1986.

*Primary Examiner*—Max Hindenburg
*Attorney, Agent, or Firm*—Burgess, Ryan & Wayne

[57] ABSTRACT

A cryogenic-and-ultrasonic scalpel includes a body, a source of ultrasonic vibrations positioned within the body, a hollow, frusto conical transformer connected to the source of ultrasonic vibrations, and a tubular heat exchanger for supplying refrigerant to the scalpel blade and draining the same therefrom the heat exchanger including inner and outer fluidly intercommunicating coaxial tubes, with the blade and the transformer connected to the outer tube, and ultrasonic vibrations being imparted to the outer tube and then to the blade through the transformer, and with refrigerant supplied through the inner tube, out from holes in the outer tube onto the inner side of the blade, and drained through the outer tube.

20 Claims, 1 Drawing Sheet

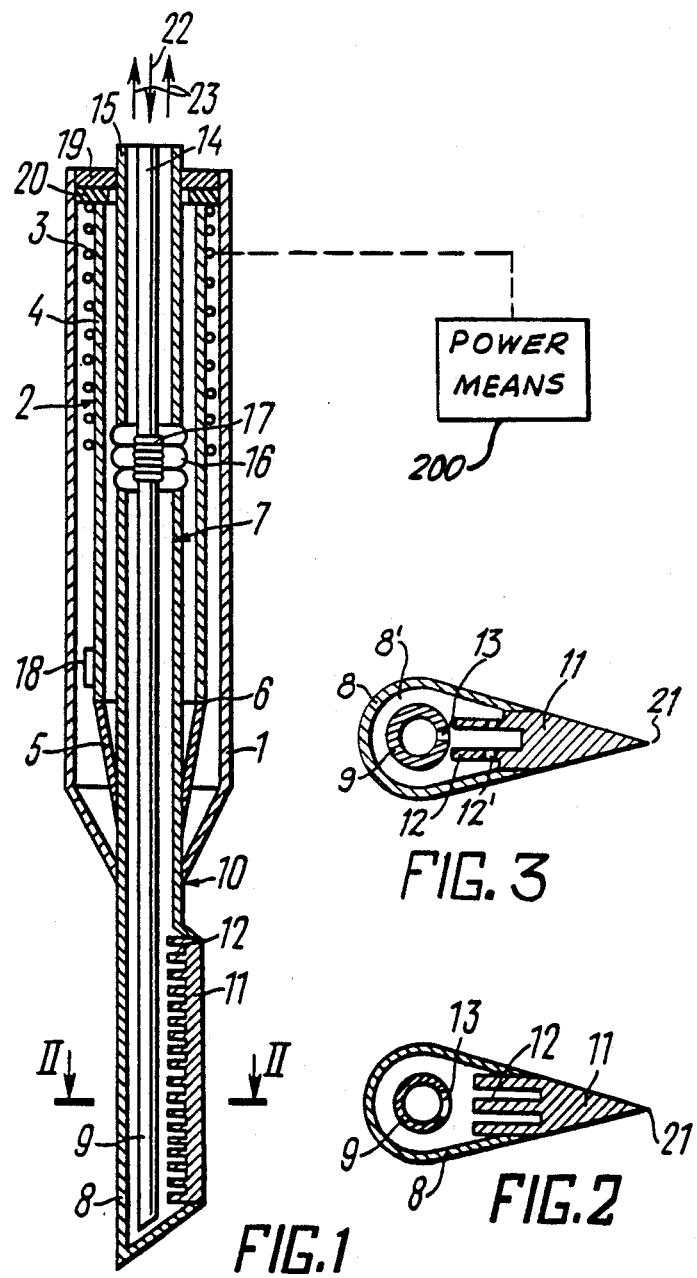

CRYOGENIC-AND-ULTRASONIC SCALPEL

REFERENCE TO RELATED APPLICATIONS

This application is a continuation-in-part of U.S. patent application Ser. No. 900,457 filed Aug. 26, 1986, entitled "CRYOGENIC-AND-ULTRASONIC SCALPEL", now U.S. Pat. No. 4,724,834.

BACKGROUND OF THE INVENTION

The invention relates generally to surgical instruments, and more specifically, is directed to cryogenic-and-ultrasonic scalpels, having particular applicability to surgery on soft tissues and parenchymatous organs, such as the liver, pancreas, kidneys, lungs, spleen, as well as in neurosurgery.

Conventional cryosurgery is directed to the use of cryogenic temperatures to freeze various tissues to destroy the tissues. However, a scalpel is generally not involved.

Thus, known in the present state of the art are cryogenic-and-ultrasonic surgical instruments, and in particular, probes which include a mechanism that joins the working portion with a source of ultrasonic vibrations, a jacket for refrigerant to pass, the jacket being interposed between the instrument base and the source of ultrasonic vibrations, and a nozzle located at the refrigerant inlet of the instrument. An example of such an instrument is described in USSR Inventor's Certificate No. 460,869.

However, the instrument is unsuitable for surgery since it is not capable of dissecting tissues, that is, there is no scalpel. Specifically, the disadvantages of such known instrument result in a low hemostatic effect due to rapid increases in the temperature of the working portion. This is caused by the fact that the base area of the instrument through which coolant streams pass, is substantially less than the area of the lateral surfaces of the working portion through which lateral surfaces heat streams pass. In addition, the heat exchanger, provided on the mechanism that connects the operating instrument with the source of ultrasonic vibrations, contributes to a decrease in the amplitude of the ultrasonic vibrations in the working portion, which causes tissue sticking to the blade and leads to a decrease in the hemostatic effect.

There is also known a cryogenic-and-ultrasonic scalpel comprising a body accommodating a source of ultrasonic vibrations, a blade connected to the source of ultrasonic vibrations through a transformer and a tubular heat exchanger for supplying refrigerant to the blade. The heat exchanger is fashioned as a U-shaped tube for providing thermal contact with the lateral surface of the blade and is connected to a refrigerant supply and removal pipes that extend through bellows located within the zone of a standing wave arising when the blade is connected to the source of ultrasonic vibrations. The tubes of the heat exchanger taper towards the cutting edge of the scalpel. An example of such an instrument is described in USSR Inventor's Certificate No. 825,056.

This instrument, however, also suffers from certain disadvantages. Specifically, disadvantages inherent in such a cryogenic-and-ultrasonic scalpel result in a low hemostatic effect and an inadequate tissue dissection rate during surgery on soft tissues and parenchymatous organs such as the liver or pancreas, due to too low refrigerating capacity of the U-shaped tubular heat exchanger. These disadvantages stem from the fact the blade features direct and thermal contact with the transformer at the point of their interconnection. In this case, a considerable part of the heat evolved by the transformer and the source of ultrasonic vibrations due to the large conversion loss of electric ultrasonic power into mechanical energy, is imparted to the blade, thus causing its temperature to rise. As a result, the refrigerating capacity of the U-shaped heat exchanger which is in thermal contact not only with the blade but also with the abundantly blood-supplied organ being operated on such as the liver, is insufficient, particularly in cases of prolonged surgery, thus causing tissue sticking to the blade, a reduced tissue dissection rate and an adversely affected hemostatic therapeutic effect. Moreover, the U-shape of the heat exchanger pipes that supplies the refrigerant renders the instrument too unwieldy, and hence, inconvenient in operation. In other words, the cryogenic material is passed over one side of the scalpel and is withdrawn after passing to the opposite side of the scalpel.

U.S. Pat. Nos. 4,528,979; 3,942,519; and 3,911,924 disclose cryogenic and ultrasonic destructors or probes. U.S. Pat. No. 3,622,755 discloses a cryogenic surgical blade. U.S. Pat. Nos. 3,888,004; 3,794,040; and 2,714,890 disclose ultrasonic blades. Other patents of interest are U.S. Pat. Nos. 3,786,814; 3,636,943; 3,918,442; and 4,609,368; and USSR Inventor's Certificates Nos. 556,797 and 1,153,901.

OBJECTS AND SUMMARY OF THE INVENTION

Accordingly, it is an object of the present invention to provide a cryogenic-and-ultrasonic scalpel, wherein the tissue being dissected does not stick to the blade while ensuring an adequate dissection rate due to the heat exchange rate and ultrasonic oscillations.

It is another object of the invention to provide a cryogenic-and-ultrasonic scalpel having a tissue dissection rate that is equal to the dissection rate obtained with a conventional scalpel.

It is still another object of the present invention to provide a cryogenic-and-ultrasonic scalpel having a greater hemostatic therapeutic effect during surgery.

It is yet another object of the present invention to provide a cryogenic-and-ultrasonic scalpel in which the temperature of the instrument is maintained below about 130° C. in order to eliminate tissue sticking to the blade.

It is a further object of the present invention to provide a cryogenic-and-ultrasonic scalpel that has a low bulk and is easy to use during a surgical operation.

It is a still further object of the present invention to provide a cryogenic-and-ultrasonic scalpel that reduces traumatic lesions inflicted upon the tissues of the organs operated upon.

It is a yet further object of the present invention to provide a cryogenic-and-ultrasonic scalpel that establishes a maximum depth of tissue freezing of about 2 mm so as to eliminate temperature traumatization of tissue.

It is another object of the present invention to provide a cryogenic-and-ultrasonic scalpel that reduces the amount of heat inflow to the blade thereby increasing the refrigerating capacity of the instrument.

It is still another object of the present invention to provide a cryogenic-and-ultrasonic scalpel that has an automatic adjustment of frequency of the ultrasonic vibrations due to a reduced loss of conversion of ultrasonic electric power into mechanical energy.

These objects are accomplished by a cryogenic-and-ultrasonic scalpel comprising a body accommodating a source of ultrasonic vibrations, a blade connected to the source of ultrasonic vibrations through a transformer, and a tubular heat exchanger for supplying refrigerant to and draining the same from the blade, the tubular heat exchanger including inner and outer coaxial fluidly intercommunicating tubes, and the transformer is connected to the outer tube of the tubular heat exchanger so as to impart ultrasonic vibrations to the outer tube and thereby to the blade which is firmly held by the outer tube.

It is expedient that the transformer be hollow and have a frusto-conical configuration with a through bore which accommodates the outer coaxially arranged tube of the tubular heat exchanger. The greater base of the frusto-conical transformer is connected to a source of ultrasonic vibrations while the lesser base is rigidly linked to the outer tube of the tubular heat exchanger so as to impart ultrasonic vibrations to the scalpel blade.

A longitudinal slit may be made in the outer tube of the tubular heat exchanger for holding the scalpel blade tightly therein while the blade surface facing into the bore of the outer tube may be shaped as at least a single-row comb.

It is desirable that holes in the inner tube of the tubular heat exchanger be directed toward the comb-shaped blade portion to maximize heat exchange.

It is also preferable that an ultrasonic vibration pickup be connected to the source of ultrasonic vibrations and be accommodated inside the body so as to provide control of the frequency of ultrasonic vibrations, the ultrasonic vibration pickup preferably being located within the antinode zone of a sound wave arising from excitation of the source of ultrasonic vibrations.

The above and other objects, features and advantages of the present invention will become readily apparent from the following detailed description which is to be read in connection with the accompanying drawings.

BRIEF DESCRIPTION OF THE DRAWINGS

FIG. 1 is a longitudinal cross-sectional view of a cryogenic-and-ultrasonic scalpel according to one embodiment of the present invention;

FIG. 2 is a cross-sectional view of the scalpel of FIG. 1, taken along line II—II thereof; and FIG. 3 is a cross-sectional view similar to that of FIG. 2, showing a modified cryogenic-and-ultrasonic scalpel according to another embodiment of the present invention.

DETAILED DESCRIPTION OF THE PREFERRED EMBODIMENTS

Referring to the drawings in detail, and initially to FIGS. 1 and 2 thereof, a cryogenic-and-ultrasonic scalpel according to one embodiment of the present invention comprises a body 1, an adjustable source 2 of ultrasonic vibrations accommodated in body 1, source 2 being provided with an energizing coil 3 and a magnetostrictive element 4 surrounded by energizing coil 3. A power means 200 supplies power to energize coil 3 at a desired frequency so as to cause vibration of magnetostrictive element 4, the rate of vibration depending upon the frequency of energization of coil 3. Source 2 is of the type described in the USSR Small Encyclopedia, "ULTRASOUND", Sovetskaya Encyclopedia Publishers, Moscow, 1979, page 196 et seq.

A transformer 5 is connected to source 2, transformer 5 being constructed as a hollow annular body and the most efficient shape of transformer or vibration transferring member 5 being frusto-conical with the greater base 6 thereof being connected to source 2. A tubular heat exchanger 7 is accommodated partially within body 1 and through a central bore of transformer 5 for supplying and withdrawing a refrigerant to the instrument, and particularly to the blade thereof. Heat exchanger 7 is constituted by at least two intercommunicating coaxial tubes or pipes 8 and 9, with the outer tube or pipe 8 being connected to the lesser base 10 of transformer 5, whereby ultrasonic vibrations are transmitted from source 2 and through transformer 5, to outer tube 8. In this regard, transformer 5 functions as an ultrasound concentrator, i e, a device adapted to increase the intensity of ultrasonic vibrations, and is preferably a rod-type concentrator, as disclosed in pages 169–172 of the aforementioned "ULTRASOUND" publication and in "REFERENCE BOOK FOR A MECHANICAL ENGINEER", Vol. 5, Book 1, Moscow 1963, page 394. Preferably, the diameter of outer tube or pipe 8 is approximately 1½ times the diameter of inner tube or feed pipe 9. For example, the diameter of inner tube 9 can be about 6 mm (but not less than about 2 mm), and the diameter of outer tube 8 can be about 10 mm. Inner tube 9 defines a feed channel therein for supplying refrigerant and outer tube 8 thereby defines a drain channel for removing the refrigerant.

It will be appreciated that heat exchanger 7 may have more than two tubes, though the number of tubes depends on requirements of the refrigerating capacity of heat exchanger 7. Thus although the accompanying drawings represent an embodiment of heat exchanger 7 incorporating two tubes, three four, or more tubes may be employed to good advantage.

A longitudinal slit is provided in outer tube 8 of heat exchanger 7 on a section thereof protruding beyond body 1, and a blade 11 is tightly held in such slit, as shown in FIG. 2 so that the cutting edge 21 thereof extends outwardly.

The surface of blade 11 (FIG. 1) that faces into the bore of outer tube 8 is shaped as at least a single-row comb 12 having a plurality of teeth ribs columns or the like, for the sake of increased contact area of blade 11 with the refrigerant. Comb 12 thereby extends into a cavity formed adjacent to the rear side of blade 11 and within the drain channel of outer tube 8. With a view to further increasing the aforesaid contact area, comb 12 may be made of a multirow design such as in three rows as shown in FIG. 2. Preferably the inside or comb part of blade 11 is made of or coated with copper, and the outside part of blade 11 is made of or coated with nickel or chromium A plurality of holes 13 are also provided in inner tube 9 of heat exchanger 7 at the level of comb 12 for the refrigerant to pass from inner tube 9 to outer tube 8 and thereby impact on blade 11. Further, inner tube 9 and outer tube 8 of heat exchanger 7 are connected respectively to inlet and outlet sleeves 14 and 15 through bellows 17 and 16, whereby the refrigerant is supplied to inner tube 9 and withdrawn from outer tube 8. Bellows 16 and 17 are manometric elastic elements commonly used in various engineering fields, as disclosed in "DESIGN OF ELASTIC ELEMENTS OF MACHINES AND INSTRUMENTS" by S. A. Ponomareva and L. Ye. Andreyeva Moscow 1980, Chapter 13, pages 283-284. The upper end of body 1 is tightly closed by a cover 19 seated on a gasket 20.

An ultrasonic vibration pickup 18 for controlling the frequency of ultrasonic vibrations is connected to source 2 (FIG. 1), and is accommodated in body 1. Pickup 18 is most efficient when installed within the antinode zone of an ultrasonic wave arising from excitation of source 2. Pickup 18 may be of the type described at page 340 of the aforementioned "ULTRASOUND" publication.

Referring to FIG. 3, there is shown a modified cryogenic-and-ultrasonic scalpel according to another embodiment of the present invention in which elements similar to those in the embodiment of FIGS. 1 and 2 are identified by the same reference numerals, and a detailed description thereof will be omitted herein for the sake of brevity. As shown, the teeth of comb 12 extend closer to inner tube 9 than the teeth in the embodiment of FIGS. 1 and 2 in order to obtain more efficient heat transfer. Specifically, only two rows of teeth are provided, extending on opposite sides of holes 13 symmetrically positioned with respect to a central, diametrical plane of the scalpel and extending a distance up to holes 13. Because of the closeness of the teeth of comb 12 to inner tube 9, it is difficult for the refrigerant to return to the portion of the cavity 8' defined between inner tube 9 and outer tube 8 at the opposite side of inner tube 9. Thus, in accordance with this embodiment of the present invention, a plurality of holes 12' are provided in the teeth of comb 12 so that the refrigerant can easily pass to all parts of cavity 8' The holes 12' are formed near the main body of blade 11 to impart maximum heat transfer.

The cryogenic-and-ultrasonic scalpels of FIGS. 1-3 are prepared for operation as follows.

The refrigerant is fed along inlet sleeve 14 through the bellows 17, in the direction of arrow 22, to the heat exchanger 7, and specifically to inner tube 9 Upon emerging from the holes 13, the refrigerant hits the teeth of comb 12 of blade 11, thereby cooling blade 11. The resultant vapour-liquid mixture is discharged from heat exchanger 7 through outer tube 8, bellows 16, and sleeve 15 as indicated by arrows 23.

The time needed to set the working temperature of the cryogenic-and-ultrasonic scalpel, when using liquid nitrogen at about 80° K. as a refrigerant, ranges between about 3 and about 5 minutes at a positive pressure in the feed reservoir within the range of about $0.2 \times 10^5$ to $0.5 \times 10^5$ Pa. During this cooling operation, blade 11 is first covered with frost, and upon reaching a temperature of about 80° K. atmospheric gases are liquified on blade 11 which is manifested by formation of a thin film of liquid air on the portion of outer tube 8 of heat exchanger 7 extending from body 1, and on blade 11.

Once the working temperature of the scalpel has been attained, source 2 of ultrasonic vibrations is energized To obtain the maximum vibration amplitude of blade 11, the frequency of source 2 is automatically adjusted for the resonant level with the aid of ultrasonic vibration pickup 18. This, in turn, leads to a maximum vibration amplitude of blade 11, thereby eliminating sticking of the tissues operated upon to blade 11, and enhances the hemostatic effect, whereupon the organ can be safely and easily operated upon.

The range of ultrasonic vibrations can vary between about 20 and about 80 kHz, and has been selected experimentally to obtain an optimum range from about 22 to about 28 kHz. Although the use of higher frequencies of ultrasonic vibrations, for example, from about 200-300 kHz, provides a greater hemostatic effect, it also causes massive heat flows which decrease the cryogenic effect of the scalpel. The main aim of using ultrasonic vibrations in the invention resides in the increase of the cryogenic hemostatic effect, but not in the hemostatic effect obtained by the ultrasonic vibrations themselves.

During the operation, the temperature of the working portion of heat exchanger 7 is maintained preferably within the range from about −100° C. to about −160° C. and the hemostatic effect of the cold is increased by ultrasonic vibrations. However, this range may vary for different operations At the normal cutting rate and when the above scalpel temperatures and frequencies of ultrasonic vibrations are used, the depth of frost penetration into tissues during the operation is from about 1.5 to about 2 mm.

In the case of surgery on the soft tissues or parenchymatous organs, the working temperature of blade 11 is approximately 120° K. since the inflow of cold to blade 11 from heat exchanger 7 exceeds the inflow of heat from the organ being operated on. A high hemostatic effect is observed even when blade 11 is introduced completely into the organ being operated on so that the tissue in contact with the portion of outer tube 8 extending from heat exchanger 7 and carrying blade 11 tightly in the longitudinal slit, is cooled at the highest rate. The tissue dissection rate is adjusted by an appropriately selected refrigerant pressure, whereby sticking of the tissue of the organ operated upon to blade 11 is eliminated. This, in turn, makes it possible to dissect tissues with the proposed cryogenic-and-ultrasonic scalpel at a rate equal to that of a conventional surgical scalpel even in cases of prolonged surgery on such organs as the liver and pancreas Further, due to the fact that blade 11 is tightly held in the longitudinal slit of outer tube 8 of heat exchanger 7, and that the blade surface facing into the bore of outer tube 8 is shaped as a multirow comb 12, the teeth of which face toward inner tube 9 of heat exchanger 7 in opposing relation to holes 13 spaced throughout the length of comb 12, a more efficient cooling of blade 11 of the cryogenic-and-ultrasonic scalpel results due to an increased area of heat transfer between the refrigerant and blade 11. Moreover by providing pickup 18 on source 2 of ultrasonic vibrations, within the antinode zone of an ultrasonic wave resulting from excitation of source 2 an automatic adjustment of the frequency of source 2 of ultrasonic vibrations is possible in the course of the scalpel operation. This in turn, results in about a 3 to about a 5 fold reduction of heat evolution from the transformer 5 (due to lower loss of conversion of ultrasonic electric power into mechanical energy), that is, this results in a decreased heat inflow to blade 11. Apart from this the tissue of the organ operated upon is prevented from sticking to blade 11, the rate of tissue dissection is increased and the therapeutic hemostatic effect is enhanced.

Still further by providing heat exchanger 7 in the shape of coaxially arranged outer tube 8 and inner tube 9, both being accommodated in the through bore of hollow transformer 5 there results a reduction in the overall dimensions of the scalpel, thereby making manipulation of the scalpel more convenient, without injuring the tissues of the parenchymatous organ being operated on. Further, no tissue sticking to blade 11 occurs the dissection rate is increased and there is a reduction of any postoperative complications Thus with the present invention there is less loss of blood due to the low temperature, a faster recovery for the patient, i.e., about a 30% less hospital stay, less of a traumatic effect since the depth of the incision is reduced, and a greater overall success in the operation.

The present cryogenic-and-ultrasonic scalpel has been tested experimentally on over twenty dogs wherein resection of different sections of the liver, spleen, kidneys and pancreas has been performed. It has been established that the present scalpel, upon reaching the working temperature, is capable of tissue dissecting at a rate of a conventional scalpel, involves no tissue sticking to blade 11 and produces a satisfactory hemostasis on parenchymatous vessels having a diameter of up to 2 mm.

With the use of the present cryogenic-and-ultrasonic scalpel seven liver resections have been performed under clinical conditions (i.e., lobectomies and halvings of the organ) for some parasitic diseases (alveolococcosis echnococcosis) and tumors, as well as for purulent processes. All experimental data characterizing the scalpel operation have been fully corroborated during the aforementioned surgery. The patients operated upon have sustained surgery successfully and recovered uneventfully. Further, a pronounced hemostatic effect has been observed during surgery (i.e., arresting of the parenchymatous bleeding). The hospitalization period of the patients has also been substantially reduced.

Having described specific preferred embodiments of the invention with reference to the accompanying drawings, it will be appreciated that the present invention is not limited to those precise embodiments, and that various changes and modifications can be effected therein by one of ordinary skill in the art without departing from the scope or spirit of the invention as defined in the appended claims.

What is claimed is:

1. A cryogenic-and-ultrasonic scalpel, comprising:
   blade means for dissecting biological tissues, said blade having a cutting edge;
   a body;
   a source of ultrasonic vibrations, said source being positioned within said body;
   a transformer positioned within said body and connected to said source of ultrasonic vibrations;
   a heat exchanger positioned within said body and including an outer tube and an inner tube arranged within said outer tube both of said tubes fluidly communicating with each other, said outer tube connected with and positioned within said transformer and said body and connected with said blade means to impart ultrasonic vibrations to said blade means through said outer tube; and
   said heat exchanger admitting a refrigerating agent to said blade means and withdrawing said agent from said blade means for cooling the latter.

2. A cryogenic and ultrasonic scalpel according to claim 1, wherein said transformer is made as a hollow annular body having a through bore coaxial with said outer tube of said tubular heat exchanger when said outer tube of said tubular heat exchanger is positioned within said through bore.

3. A cryogenic-and-ultrasonic scalpel according to claim 2, wherein said transformer has a hollow, frustoconical configuration with a greater and a lesser base, said greater base being connected to said source of ultrasonic vibrations and said lesser base being connected to said outer tube of said heat exchanger so as to impart vibrations to said blade means.

4. A cryogenic-and-ultrasonic scalpel according to claim 2, wherein a longitudinal slit is made in said outer tube of said heat exchanger, and said blade means is tightly held in said longitudinal slit with said cutting edge extending outwardly.

5. A cryogenic-and-ultrasonic scalpel according to claim 1, wherein a longitudinal slit is made in said outer tube of said heat exchanger and said blade means is tightly held in said longitudinal slit with said cutting edge extending outwardly.

6. A cryogenic and ultrasonic scalpel according to claim 1, comprising an ultrasonic vibration pickup positioned inside said body for controlling the frequency of ultrasonic vibrations by said source of ultrasonic vibrations.

7. A cryogenic-and-ultrasonic scalpel according to claim 6, wherein said source of ultrasonic vibrations establishes an antinode zone of an ultrasonic wave, and said ultrasonic vibration pickup is located within said antinode zone.

8. A cryogenic-and-ultrasonic scalpel according to claim 1, wherein said blade means has an inner surface that faces into said outer tube of said heat exchanger, and at least a single-row comb is provided on said inner surface of said blade means.

9. A cryogenic and ultrasonic scalpel according to claim 8, wherein said inner tube of said heat exchanger has a plurality of holes which face toward said at least single-row comb.

10. A cryogenic-and-ultrasonic scalpel comprising:
    a blade having a cutting edge and an opposite rear side;
    a source of ultrasonic vibrations;
    a transformer for supplying said ultrasonic vibrations from said source to said blade; and
    a heat exchanger for cryogenically cooling said blade, said heat exchanger including a feed channel and a drain channel for a refrigerating agent, said drain channel including a cavity formed adjacent the rear side of said blade and said feed channel includes a feed pipe projecting into said drain channel and from which the refrigerating agent is supplied.

11. A cryogenic-and-ultrasonic scalpel according to claim 10 wherein said feed pipe includes an axially extending slit opening distributed over the length of said blade, from which said refrigerating agent issues in the direction of said cutting edge.

12. A cryogenic-and-ultrasonic scalpel according to claim 10, wherein said drain cavity is formed by an outer pipe surrounding said feed pipe and having an axial slit in which said blade is held.

13. A cryogenic-and-ultrasonic scalpel according to claim 12, wherein said transformer is attached to said outer pipe.

14. A cryogenic-and ultrasonic scalpel according to claim 13, wherein said transformer is shaped as a hollow annular body into which coaxially extends said outer pipe and said feed pipe is inserted in said outer pipe.

15. A cryogenic-and-ultrasonic scalpel according to claim 14, wherein said transformer is shaped as a hollow cone frustum having its greater base attached to said source of vibrations and having its lesser base attached to said outer pipe.

16. A cryogenic-and ultrasonic scalpel according to claim 10, wherein surface-enlarging ribs are formed on the rear side of said blade.

17. A cryogenic-and-ultrasonic scalpel according to claim 16, wherein said ribs extend in an axial direction of said scalpel.

18. A cryogenic-and-ultrasonic scalpel according to claim 17, wherein two ribs are provided symmetrically positioned with respect to a central plane of said scalpel and extend between said drain pipe and said slit opening, said ribs forming a groove therebetween and have side openings therein at the bottom of said groove through which the refrigerating agent issues from said groove to supply other ribs and said cavity 19. A cryogenic-and-ultrasonic scalpel according to claim 10 wherein said rear side of said blade has individually jutting surface enlarging columns.

20. A cryogenic-and-ultrasonic scalpel, comprising:
- a blade having a cutting edge used to dissect biological tissues;
- a body;
- a source of ultrasonic vibrations positioned within said body;
- a transformer positioned within said body and made as a hollow cone frustum having a greater base, a lesser base, and a through bore said greater base being connected to said source of ultrasonic vibrations;
- a heat exchanger positioned within said body and comprising an outer tube and an inner tube, both fluidly communicating with each other when said inner tube is coaxial with said outer tube said heat exchanger supplying a refrigerating agent to and withdrawing it from said blade for cooling the latter;
- said outer tube of said heat exchanger arranged coaxially in said through bore of said transformer and connected to said lesser base of said transformer so as to impart ultrasonic vibrations to said blade, a longitudinal slit formed in said outer tube and said blade held in said longitudinal slit with said cutting edge extending outwardly therefrom; and
- said blade having an inner surface that faces into said outer tube of said heat exchanger, and at least a single-row comb provided on said inner surface of said blade.

* * * * *